(12) United States Patent
Lu et al.

(10) Patent No.: US 9,357,955 B2
(45) Date of Patent: Jun. 7, 2016

(54) PORTABLE ANALYTICAL DEVICE AND SYSTEM

(71) Applicant: Industrial Technology Research Institute, Hsinchu (TW)

(72) Inventors: Hui-Hsin Lu, New Taipei (TW); Sheng-Po Wang, Taoyuan County (TW); Mao-Yin Wang, New Taipei (TW); Kuan-Hung Chou, Changhua County (TW); Ching-Kai Peng, Hsinchu (TW); Wei-Chin Huang, Tainan (TW); Yu-Hsuan Liao, Taipei (TW); Louis Lu-Chen Hsu, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 14/221,300

(22) Filed: Mar. 21, 2014

(65) Prior Publication Data

US 2015/0265193 A1 Sep. 24, 2015

(51) Int. Cl.
*G01N 33/48* (2006.01)
*A61B 5/1455* (2006.01)
*G01N 21/41* (2006.01)
*G01N 21/03* (2006.01)
*G01N 21/31* (2006.01)
*A61B 5/024* (2006.01)
*A61B 5/145* (2006.01)

(52) U.S. Cl.
CPC ............ *A61B 5/14551* (2013.01); *G01N 21/03* (2013.01); *G01N 21/314* (2013.01); *G01N 21/4133* (2013.01); *A61B 5/02438* (2013.01); *A61B 5/14546* (2013.01); *A61B 2562/146* (2013.01); *G01N 2201/0221* (2013.01)

(58) Field of Classification Search
CPC .............. G01N 21/03; G01N 21/0303; G01N 2021/035; G01N 2201/08; G01N 2021/0346; G01N 2021/036
See application file for complete search history.

(56) References Cited

U.S. PATENT DOCUMENTS

| 4,880,304 A | 11/1989 | Jaeb et al. |
| 7,375,815 B2 * | 5/2008 | Kralik ........................... 356/440 |
| 7,491,366 B2 | 2/2009 | Tokhtuev et al. |
| 8,039,144 B2 | 10/2011 | Louie |

(Continued)

FOREIGN PATENT DOCUMENTS

| CN | 101319993 | 12/2008 |
| CN | 202374312 | 8/2012 |

(Continued)

OTHER PUBLICATIONS

Keally et al., "PBN: Towards Practical Activity Recognition Using Smartphone-Based Body Sensor Networks," Proceedings of the 9th ACM Conference on Embedded Networked Sensor Systems, Nov. 1-4, 2011, pp. 246-259.

(Continued)

*Primary Examiner* — Michael P Stafira
(74) *Attorney, Agent, or Firm* — Jianq Chyun IP Office (57) ABSTRACT

A portable analytical device including at least one optical unit and optionally an adapting device are provided. The optical unit includes a light beam receiving area, a sample holder, a light beam exiting area, and a lens component. The adapting device holds the optical unit and an external hand-held computing device (EHCD), such that the optical unit is coupled to the EHCD.

33 Claims, 8 Drawing Sheets

(56) References Cited

U.S. PATENT DOCUMENTS

| | | | |
|---|---|---|---|
| 8,078,250 | B2 | 12/2011 | Chen et al. |
| 8,239,144 | B2 | 8/2012 | Fedele |
| 8,321,004 | B2 | 11/2012 | Moon et al. |
| 2006/0198761 | A1 | 9/2006 | Tokhtuev et al. |
| 2010/0081892 | A1 | 4/2010 | Sethi et al. |
| 2010/0166252 | A1 | 7/2010 | Ahmed et al. |
| 2012/0053433 | A1 | 3/2012 | Chamoun et al. |
| 2012/0108927 | A1 | 5/2012 | Chen et al. |
| 2012/0296219 | A1 | 11/2012 | Chon et al. |

FOREIGN PATENT DOCUMENTS

| | | |
|---|---|---|
| TW | 200412427 | 7/2004 |
| TW | I335426 | 1/2011 |
| TW | M445429 | 1/2013 |
| TW | 201322143 | 6/2013 |

OTHER PUBLICATIONS

Zhong et al., "A Phone-Centered Body Sensor Network Platform: Cost, Energy Efficiency & User Interface," BSN 2006 International Workshop on Wearable and Implantable Body Sensor Networks, Apr. 3-5, 2006, pp. 1-4.

Kulkarni et al., "Smartphone Driven Healthcare System for Rural Communities in Developing Countries," Proceedings of the 2nd International Workshop on Systems and Networking Support for Health Care and Assisted Living Environments, Jun. 2008, pp. 1-3.

Scully et al., "Physiological Parameter Monitoring from Optical Recordings With a Mobile Phone," IEEE Transactions on Biomedical Engineering, Feb. 2012, pp. 303-306.

Khandoker et al., "Smartphone-based low cost oximeter photoplethysmography," 6th International Conference on Electrical and Computer Engineering ICECE 2010, Dec. 18-20, 2010, pp. 634-637.

Mehta et al., "Mobile Voice Health Monitoring Using a Wearable Accelerometer Sensor and a Smartphone Platform," IEEE Transactions on Biomedical Engineering, Nov. 2012, pp. 3090-3096.

Ko et al., "Wireless Sensor Networks for Healthcare," Proceedings of the IEEE, Nov. 2010, pp. 1947-1960.

Gregoski et al., "Development and Validation of a Smartphone Heart Rate Acquisition Application for Health Promotion and Wellness Telehealth Applications," International Journal of Telemedicine and Applications, Jan. 2012, pp. 1-7.

Muaremi et al., "Monitor and Understand Pilgrims: Data Collection using Smartphones and Wearable Devices," Proceedings of the 2013 ACM conference on Pervasive and ubiquitous computing adjunct publication, Sep. 8-12, 2013, pp. 679-688.

Hudson et al., "Usability testing of a prototype Phone Oximeter with healthcare providers in high- and low-medical resource environments," Anaesthesia, Sep. 2012, pp. 957-967.

\* cited by examiner

PORTABLE ANALYTICAL DEVICE AND SYSTEM

TECHNICAL FIELD

This disclosure generally relates to portable analytical devices and systems for measuring optical properties of a sample.

BACKGROUND

There are a variety of instruments available for measuring the properties of a sample. For example, an oximeter is used for measuring the amount of saturated hemoglobin in tissue capillaries of a person, and a refractometer is used for determining the concentration of a dissolved substance in a liquid sample.

SpO2, which has been viewed as the 'fifth vital sign', represents blood oxygen saturation. Medical professionals can detect hypoxemia, i.e. deficiency of oxygen, by monitoring a patient's SpO2. Values between about 95-100% are considered normal; for those below this level indicate hypoxemia.

Pulse oximetry is a technique for measuring the SpO2 of a patient. This parameter is obtained from the patient's arterial oxygen saturation, or SaO2, which is a percentage of oxygenated arterial hemoglobin presents in the patient's blood.

In general, functional hemoglobin molecules can bind with up to four oxygen molecules to yield 'oxygenated' hemoglobin (HbO2). A hemoglobin molecule bound with less than four oxygen molecules is classified as 'reduced' hemoglobin (Hb). Conventional pulse oximeters use algorithms that assume only HbO2 and Hb are present in the blood, and measure SpO2 from the ratio of oxygenated hemoglobin to the total amount of hemoglobin (both oxygenated "HbO2" and reduced "Hb") according to equation (1):

$$SpO2=HbO2/(HbO2+Hb) \quad (1)$$

HbO2 and Hb levels appear can be measured optically in different absorption spectra, e.g. visible-red and infrared regions, respectively. Conventional pulse oximeters carry light sources that radiate in the visible-red ($\lambda$, of ~660 nm) and infrared ($\lambda$, between 900 and 950 nm) spectral regions. They also carry a photodetector for measuring a portion of radiation at each mentioned wavelength that transmits through the patient's pulsating blood.

At 660 nm, for example, Hb absorbs about ten times as much radiation as HbO2, whereas at 925 nm HbO2 absorbs about two times as much radiation as Hb. Detection of transmitted radiation at these wavelengths yields two time-dependent waveforms, each called a photoplethysmogram (PPG), which are used by an oximeter to solve for a SpO2 value as defined in equation (1) above.

Specifically, the oximeter processes two PPG waveforms, one is measured with red (RED(PPG)) and the other one is infrared (IR(PPG)) wavelengths to determine time-dependent AC signals and time-independent DC signals. The AC component is mainly caused by pulsatile changes in arterial blood volume. The frequency of the AC component is equivalent to the patient's heart beat rate. Therefore, the heart beat rate can be estimated directly from counting the frequency of the AC component. The term "AC signals", refers to a portion of a PPG waveform that varies relatively rapidly with time, e.g. the portion of the signal originating by pulsations in the patient's blood. The term "DC signals", in contrast, is a portion of the PPG that is relatively invariant with time, e.g. the portion of the signal originates from scattering off of components such as bone, skin, and non-pulsating components of the patient's blood.

Separation of AC and DC signals is typically done with both analog and digital filtering techniques that are well-known in the art. During pulse oximetry, a normalized "R value" is typically calculated from AC and DC signals using equation (2), below:

$$R=(Red(AC)/Red(DC))/(IR(AC)/IR(DC)) \quad (2)$$

R, represents a ratio of Hb to HbO2. It equates an actual SpO2 value, which ranges from 0%~100% O2, to an empirical relationship that resembles a non-linear equation. Above about 70% O2, this equation typically yields values that are accurate to a few percent. Measurements below this value, while not necessarily accurate, still indicate a patient who is in need of medical attention.

A refractometer is utilized by emitting a light beam through a sample solution and observing the refracted angle with a preset scale. The amount of the dissolved substances in the sample solution changes the optical properties of the solution in terms of refractive index. When the light passes from air to the sample solution, the speed of light becomes slower and its direction is refracted. As the amount of substance dissolved in the solution is increased, the speed of light becomes slower such that the refracted angle changes more. Specifically, in a refractometer, light from a light source is incident on a sample of index that is smaller than a prism index. The light source is diffused so rays are incident on the sample at all angles, up to a grazing incidence. In particular, the ray at the grazing incidence is refracted into the prism at a critical angle, and has the smallest angle of refraction of all other rays at a light exiting face of the prism. The result of this is that the ray at the critical angle defines a shadow boundary when looking through a telescope at the light leaving the prism. By measuring the angle between the shadow boundary and the normal to the light exiting face of the prism, the refractive index of the sample may be calculated.

Both oximeter and refractometer instruments need a plurality of light sources with at least one wavelength, complicated optical elements, and at least one detector for analytical applications, a computing device is also needed to be installed with at least one testing program. To execute measuring procedures, it includes triggering light beams, determining the signal levels, calculating test results, and outputting the testing results, etc. Therefore, the existing instruments are normally bulky, hard to operate, and expensive. Generally, each of these instruments is customized for a specific testing, or for a single-purpose testing.

SUMMARY

The proposal discloses a relatively simple portable device including an optical unit which can be used in combination with an external hand-held computing device such as a Smartphone for analytical purposes. Such device can be used to measure the amount of saturated hemoglobin in tissue capillaries of a person in a similar way as a stand alone oximeter. With the same set up, it can also be used to determine the concentration of a dissolved substance in a liquid sample in a similar way as a standalone refractometer. It can also be used to measure a person's heart beat.

In an embodiment, the optical unit includes a first light beam receiving area, a sample holder, a first light beam exiting area, and a lens component with a first reflected surface and a second reflected surface. The first reflected surface is adapted to change the light path of a first light beam from the light beam receiving area to the second reflected surface. The second reflected surface is adapted to redirect the first light beam to the first light beam exiting area. The sample holder is located on the light path of the first light beam.

In the embodiment, a portable analytical device may include an optical unit and an adapting device. The adapting device is a holder, having a first site for holding an external hand-held computing device and a second site for positioning the optical unit to the external hand-held computing device such that the optical unit is aligned with the EHCD.

In another embodiment, a portable analytical system for measuring physiological parameters includes an input device for receiving data, a first emitter, a second emitter, a memory storing information, an output device for displaying the calculated the physiological parameters and a processing unit coupled to the input device, the output device, and the memory for controlling the execution of the program routines. The memory storing information includes a plurality of testing program routines. The testing program routines include triggering a first emitting module for controlling the first emitter to emit a first light beam with a first wavelength and triggering a second emitting module for controlling the second emitter to emit a second light beam with a second wavelength toward a sample, activating a recorder for recording a plurality of signals resulted from the first light beam and the second light beam received from the sample with a predetermined duration, and enabling a calculator for calculating a plurality of physiological parameters based on the recorded signals.

In another embodiment, a method for measuring the level of saturated hemoglobin includes steps of: (a) illuminating a first light beam of a first wavelength and a second light beam of a second wavelength from an external hand-held computing device to a sample; (b) establishing an acquisition time to collect signals from the sample; (c) receiving a plurality of signals from the first light beam and the second light beam penetrating or reflected from the sample by a plurality of receivers in the external hand-held computing device, wherein a measurement is executed on the external hand-held computing device and (d) comparing intensity of each of the received signals to predefined signals. If the intensities of the received signals are greater than the predefined signals, then a level of saturated hemoglobin is calculated by using the formula (1). If the intensities of the received signals are less than the predefined signals, the acquisition time in step (b) is extended and the steps (c)-(d) are repeated. Finally, (e) outputting the level of saturated hemoglobin on a display of the external hand-held computing device.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DESCRIPTION OF EMBODIMENTS

Referring now to the drawings, wherein identical or corresponding parts are identified with the same reference numerals, numerous embodiments of the disclosure are illustrated. It is within the scope of the disclosure to interchange different parts and components of one or more illustrated embodiments for another, as would be apparent to those skilled in the art.

Figure 1A:
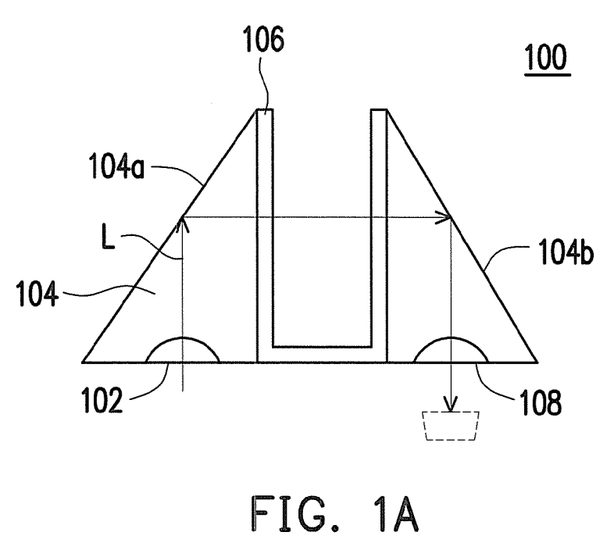
FIG. 1A is a cross-sectional view of an optical unit according to a first embodiment of the disclosure.
Figure 1B:
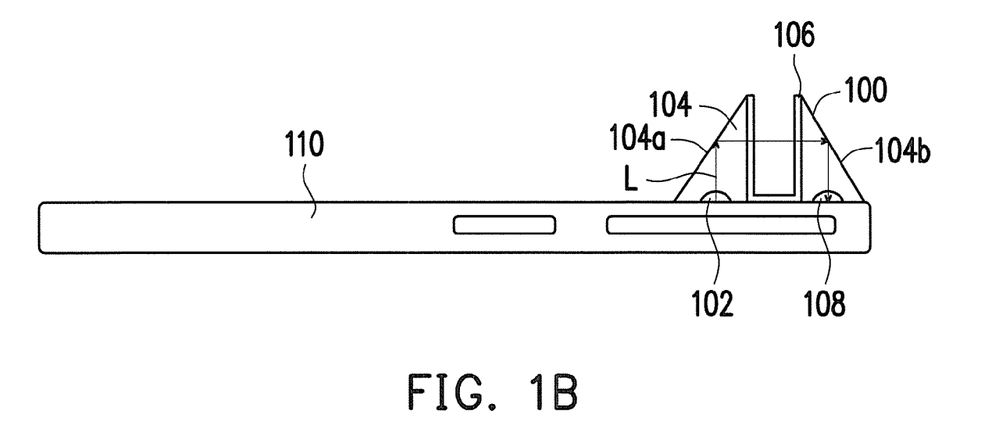
FIG. 1B is a cross-sectional view of the optical unit of the first embodiment of the disclosure disposed on an external hand-held computing device.
Figure 2:
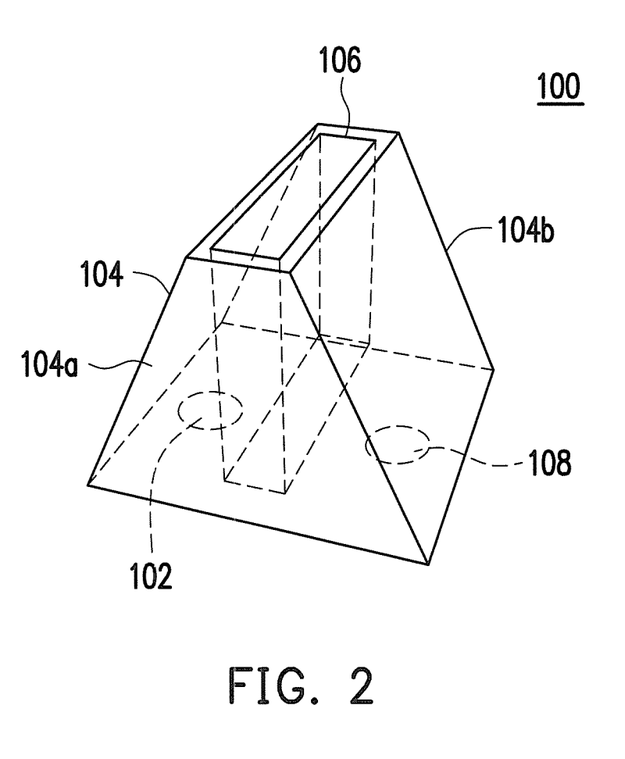
FIG. 2 is a perspective view of the optical unit according to the first embodiment of the disclosure.

FIG. 1A is a cross-sectional view of an optical unit according to a first embodiment of the disclosure. FIG. 1B is a cross-sectional view of the optical unit of the first embodiment of the disclosure disposed which is mounted on an external hand-held computing device, such as a Smartphone. FIG. 2 is a perspective view of the optical unit according to the first embodiment of the disclosure as shown in FIG. 1A. The optical unit 100 may include a light beam receiving area 102, a lens component 104, a sample holder 106 and a light beam exiting area 108. An example of light path is shown in FIG. 1A. The material of the optical unit 100 may comprise mirror-like coating, glass, plastics, quartz, and liquid. For example, the optical unit 100 may also be a liquid lens using the concept of electrowetting, wherein the lens contains two liquids, oil and water, which are immiscible. The shape of the oil drop is changed by electrowetting. Both liquids are transparent, with different indices of refraction but exactly the same density.

The light beam receiving area 102 may be used to receive a light beam L (FIG. 1A) emitted from a light beam emitter (not shown) of an external hand-held computing device 110 (FIG. 1B), such as a Smartphone, laptop computer, smart watch, and tablet. A couple of wavelength ranges of the light beam L received from the light beam emitter of the external hand-held computing device 110 for oximeter and refractometer applications (e.g. calculating the sweetness or saltiness of a sample) can be ranged from about 550 nm to about 700 nm or from about 800 nm to about 1000 nm. Furthermore, the light beam receiving area 102 may be coupled to, or aligned to, a light beam emitter (not shown) of the external hand-held computing device 110. The sample holder 106 is used to hold a sample such as a liquid, a finger, or a tube containing a sample for testing. Although there are many different kinds of the external hand-held computing device, for example, it can be a Smart phone, a laptop, a camera, a CD player, a PDA, a Smart watch, or any other portable digital equipment. For simplicity, from hereon the external hand-held computing device is named as EHCD.

The EHCD 110 may comprise a camera, display or other light emitting device to serve as the light beam emitter. The light beam exiting area 108 is the place where the light beam L leaving the optical unit 100. Furthermore, the light beam exiting area 108 may be coupled, or aligned, to a light beam receiver of the EHCD 110. The EHCD 110 may further comprise an optical sensor, for example a proximity sensor, image sensor for detecting a nearby object to serve as the light beam receiver.

As shown in FIG. 1A, the optical unit 100 is designed such that the light beam L is guided from the light beam receiving area 102 to the light beam exiting area 108. The light path of the light beam comprises following sessions: (1) being received in the light beam receiving area 102, (2) illuminating at and reflecting from a first reflected surface 104a, (3) passing through the sample holder 106, (4) illuminating at and reflecting from a second reflected surface 104b, and (5) transmitting to the light beam exiting area 108. The lens component 104 in this example has a first reflected surface 104a and a second reflected surface 104b. These two surfaces can be transflective surfaces, reflective surfaces, or a combination thereof. A transflective surface allows light to partially transmit and partially reflect. Because of the first reflected surface 104a and the second reflected surface 104b of the optical unit 100, the light path of the light beam L emitted from an emitter of the EHCD 110 to the optical unit 100 and return to a receiver of the EHCD 110. When the light beam L returns to the EHCD 110, the EHCD 110 may record the signals from the light beam L, and calculate the parameters of the sample according to the signals. Then the EHCD 110 can display the calculated results. Additionally, at least one of the light beam receiving area 102 and exiting area 108 may provide filtering and/or polarizing function for the light beam.

The sample holder 106 shown in FIG. 1 is located on the light path of the light beam L. However, in other arrangements it is possible that the sample holder may not be necessary located in middle of the first reflected surface 104a and the second reflected surface 104b. For example, the sample holder 106 for holding a sample (e.g. finger) can be located just on either the first reflected surface 104a or the second reflected surface 104b. The shape of the sample holder 106 may be but is not limited to a cylindrical, rectangular, bell-shaped, conical, cubical, pyramidal, or polygonal shape. For refractometer application, the direction of the light path of the light beam L is not normal to the surface of sample holder 106.

In addition, the optical unit 100 may further include a first collimator (not shown), which is provided in the light beam receiving area 102 for collimating the incoming light beam L from the light beam receiving area 102. The optical unit 100 may also include a second collimator (not shown), which is provided in the light beam exiting area 108 for collimating the outgoing light beam L reflected from the second reflected surface 104b.

Furthermore, the optical unit 100 may receive an additional light beam (not shown) with a different wavelength. The sample holder 106 is also located in the path of the additional light beam. Thus, when a sample is placed into the sample holder 106, optical properties of the sample through the light beam L and the additional light beam with different wavelengths passing through the sample are analyzed by the EHCD. This way, a level of saturated hemoglobin is determined through acquiring data from the two light beams with different wavelengths.

Figure 3A:
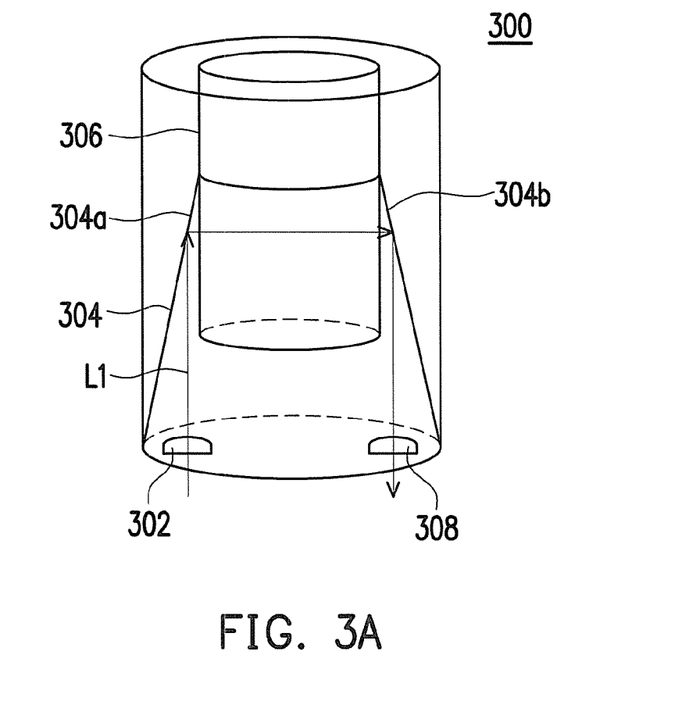
FIG. 3A is a perspective view of an optical unit according to a second embodiment of the disclosure for receiving a light beam with a first wavelength.

FIG. 3A is a perspective view of an optical unit 300 according to a second embodiment of the disclosure for receiving a light beam with a first wavelength. In this embodiment, a cylindrical shape optical unit 300 includes a conical shape lens component 304 and a cylindrical shape sample holder 306 is illustrated. The optical unit 300 is designed such that a light beam L1 is guided from the light beam receiving area 302 to the light beam exiting area 308. The light path of the light beam L1 comprises following sessions: (1) being received in the light beam receiving area 302, (2) illuminating at and reflecting from a first reflected surface 304a, (3) passing through the sample holder 306, (4) illuminating at and reflecting from a second reflected surface 304b, and (5) transmitting to the light beam exiting area 308.

In this example, the lens component 304 has a first reflected spot 304a and a second reflected spot 304b. In fact, these two spots are located on the same surface of the conical shape lens component 304. The lens surface may be a transflective surface, a reflective surface, or a combination thereof. A transflective surface allows light to partially transmit and partially reflect.

Figure 3B:
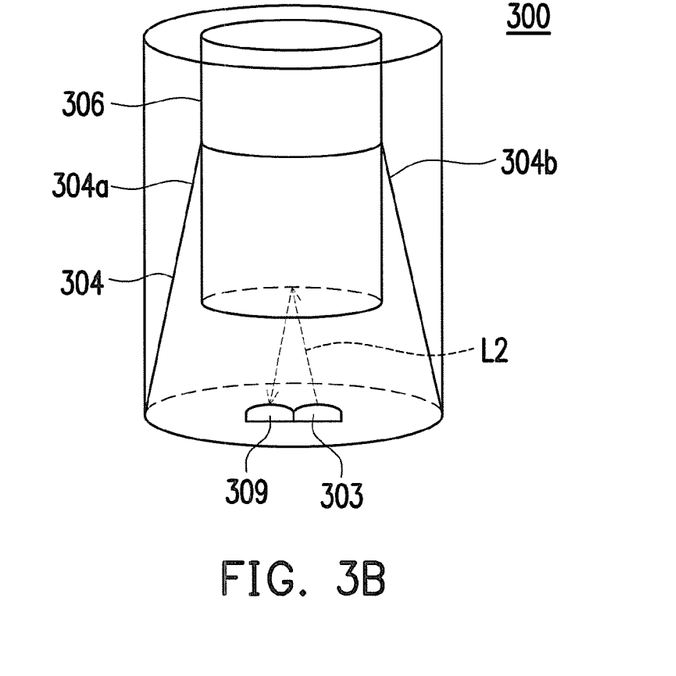
FIG. 3B is a perspective view of the optical unit according to the second embodiment of the disclosure for receiving another light beam with a second wavelength.

FIG. 3B is a perspective view of the optical unit according to the same second embodiment of the disclosure for receiving another light beam with a second wavelength. The light beam receiving area 303 and the light beam exiting area 309 are shown in FIG. 3B. The light path of another light beam L2 of the optical unit 300 comprises following sessions: (1) being received in a light beam receiving area 303, (2) illuminating at and passing through the sample holder 306, and (3) transmitting a reflected light beam to a light beam exiting area 309.

When a sample is placed into the sample holder 306, optical properties of the sample through the light beams L1 and L2 with different wavelengths reflected from the sample are analyzed by the EHCD. In this embodiment, a level of saturated hemoglobin is determined through acquiring data from the light beam L1 and the light beam L2.

In other embodiments, the optical unit 300 can utilize only one set of the light beam receiving area 302 and the light beam exiting area 308, or the light beam receiving area 303 and the light beam exit area 309. By having just one set of the light beam receiving area and the light beam exiting area, only one light beam is measured, which can be used to measure, for example, the saltiness or sweetness of a sample. In this case, the direction of the light path of the light beams L1 and L2 are not normal to the surface of sample holder 306 for the application of refractometer.

Figure 4:
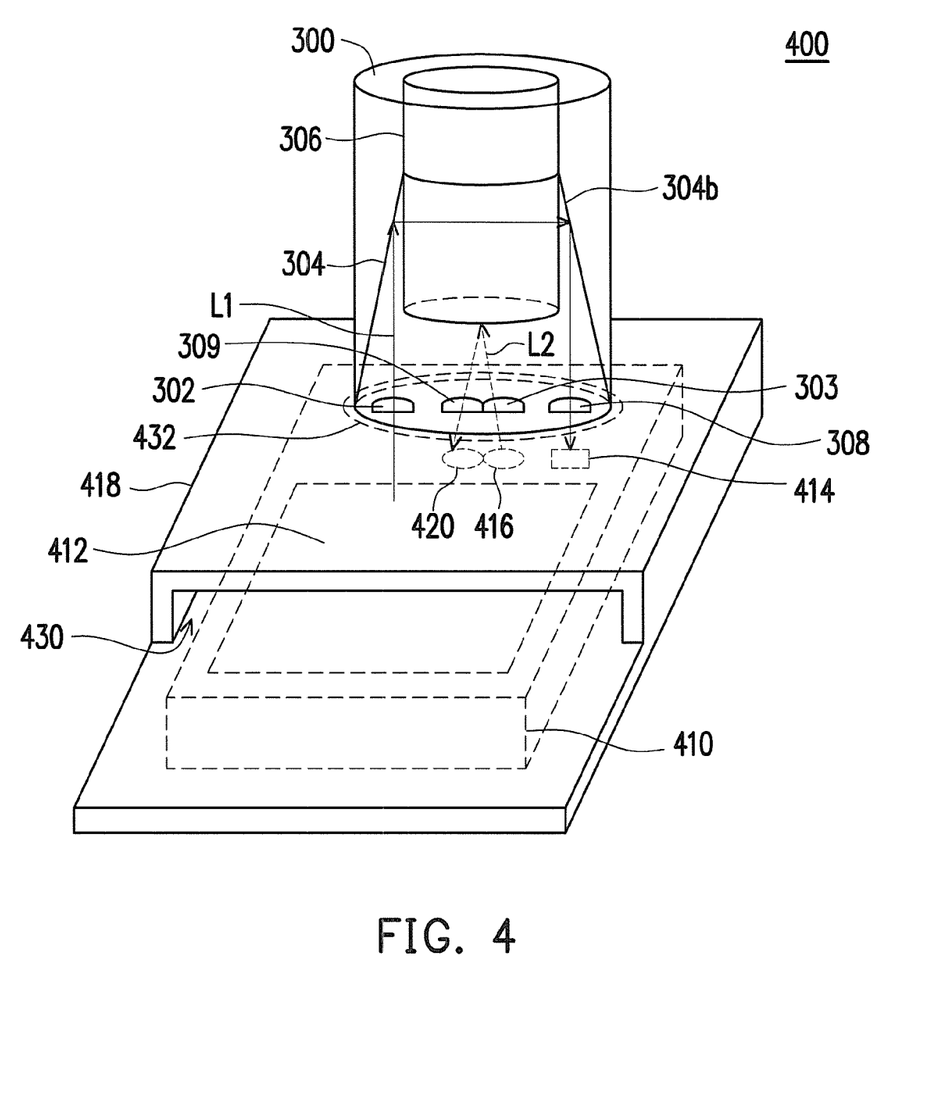
FIG. 4 is a perspective view of a portable analytical device with an adaptive device, the optical unit of FIG. 3A and FIG. 3B, and an external hand-held computing device according to the second embodiment of the disclosure.

FIG. 4 is a perspective view of the portable analytical device 300 which is used in combination with an adaptive device 418. In this embodiment, the optical unit 300 (from either FIG. 3A and FIG. 3B) and an EHCD 410 are aligned to each other. Here the portable analytical device 400 comprises an optical unit 300 and an adapting device 418. The adapting device 418 haves a first site 430 for holding the EHCD 410 and a second site 432 for holding the optical unit 300, such that the optical unit 300 is aligned to the EHCD 410. It can be seen in FIG. 4 that the first site 430 is the space in the adapting device 418 holding the EHCD 410, and the second site 432 is the area on the adapting device 418 holding the optical unit 300. The first light beam emitter 412 (e.g. a display unit) of the EHCD 410 is aligned with the first light beam receiving area 302 of the optical unit 300. The first light beam receiver 414 (e.g. a camera) of the EHCD 410 is aligned with the first light beam exiting area 308 of the optical unit 300. The second light beam emitter 416 (e.g. a proximity sensor) of the EHCD 410 is aligned with the second light beam receiving area 303 of the optical unit 300. The second light beam receiver 420

(e.g. the proximity sensor) of the EHCD 410 is aligned with the second light beam exiting area 309 of the optical unit 300.

In one embodiment, a first collimator (not shown) may be coupled to at least one corresponding light beam emitter of the EHCD 410 and a second collimator (not shown) may be coupled to at least one corresponding light beam receiver of the EHCD 410. The EHCD 410 may record the signals from the light beams, calculate the data based on the signals, and display the results. The portable analytical device 400 may also be used as a refractometer for analyzing optical properties such as sweetness, saltiness of a sample. Alternatively, the portable analytical device 400 may be an oximeter for analyzing the saturated hemoglobin or heart beat rate of a patient.

Figure 5:
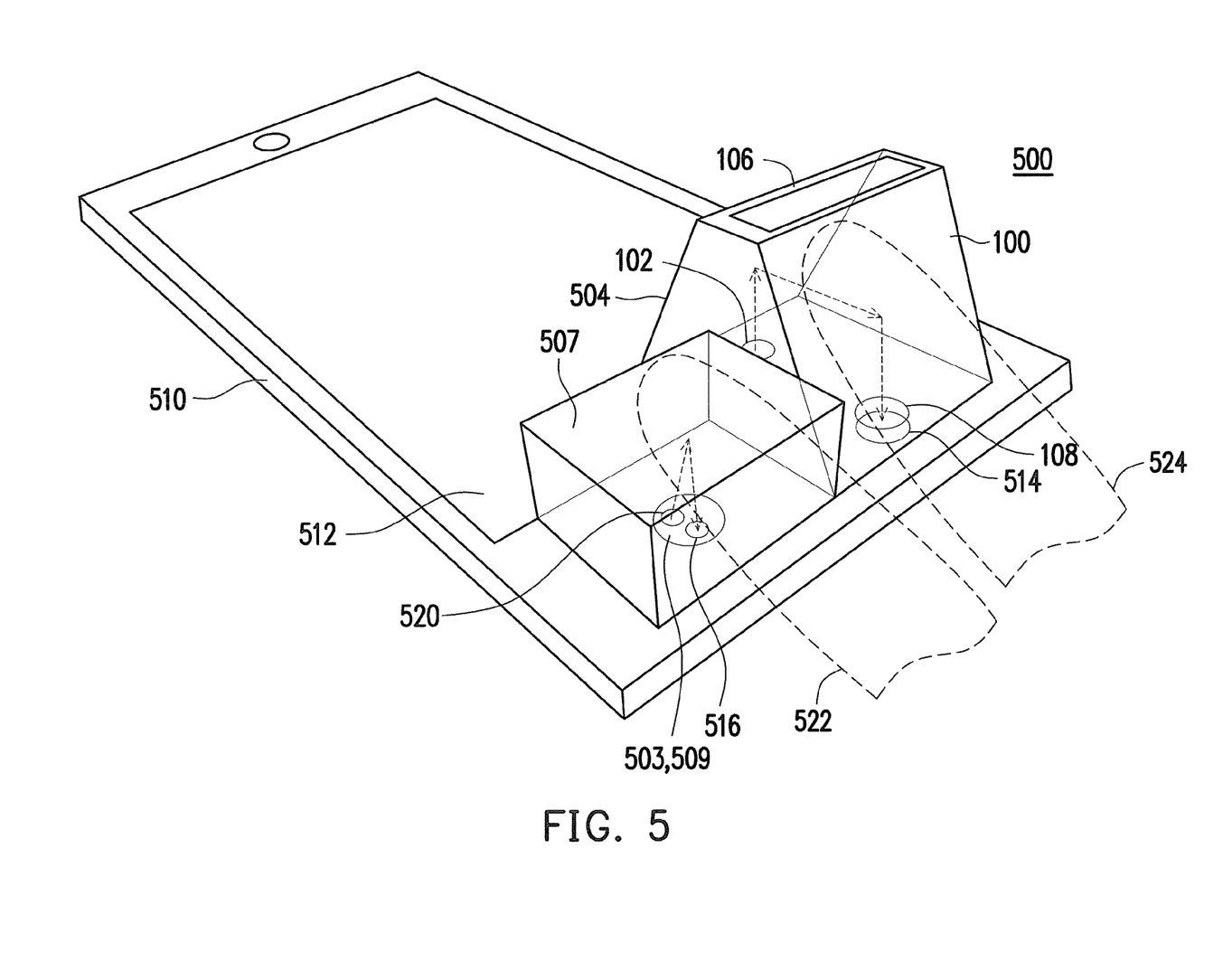
FIG. 5 is a perspective view of a portable analytical device by using the optical unit of FIG. 1A, an additional sample holder, and an external hand-held computing device for dual-finger analysis according to a third embodiment of the disclosure.

FIG. 5 is a perspective view of a portable analytical device by using the optical unit 100 (as shown in FIG. 1 and FIG. 2), an additional sample holder 507, and an EHCD 510 for dual-finger analysis according to a third embodiment of the disclosure. In the portable analytical device 500, the first light beam receiving area 102 of the optical unit 100 is aligned to receive a light beam from a first light beam emitter 512 (a display) of the EHCD 510. The first light beam exiting area 108 of the optical unit 100 is aligned to a first light beam receiver 514 (a camera) of the EHCD 510. A first sample (or finger) 524 is placed on a first sample holder 106, which is formed on the second reflecting surface 104b of the optical unit 100. A second sample (or finger) 522 is placed on a second sample holder 507. The second sample holder 507 is disposed above a second light beam emitter 516 and a second light beam receiver 520 (a proximity sensor) of the EHCD 510. The second sample 522 is placed on the second sample holder 507 for a light beam to pass through or reflect from the second sample 522 from a second light beam receiving area 503. The light beam is received by the EHCD 510 by passing through a second light beam exiting area 509 of the second sample holder 507. In this embodiment, the second light beam receiving area 503 and the second light beam exiting area 509 are located approximately the same area. In other embodiments, the second light beam receiving area 503 and the second light beam exiting area 509 may also be located at different areas. Optionally, the second sample holder 507 can be omitted, so that the second sample 522 can be directly disposed upon the second light beam emitter 516 and the second light beam receiver 520 areas. The first sample 524 and the second sample 522 of the embodiment can be, for example, two different fingers of a user.

In the embodiment, the first light beam emitter 512 and the second light beam emitter 516 emit light beams with two different wavelengths for measuring physiological data such as a level of saturated hemoglobin. Alternatively, only one light beam emitter may be used to emit just one wavelength, to detect physiological data requiring only one wavelength, or to measure the sweetness and saltiness of a sample.

Figure 6:
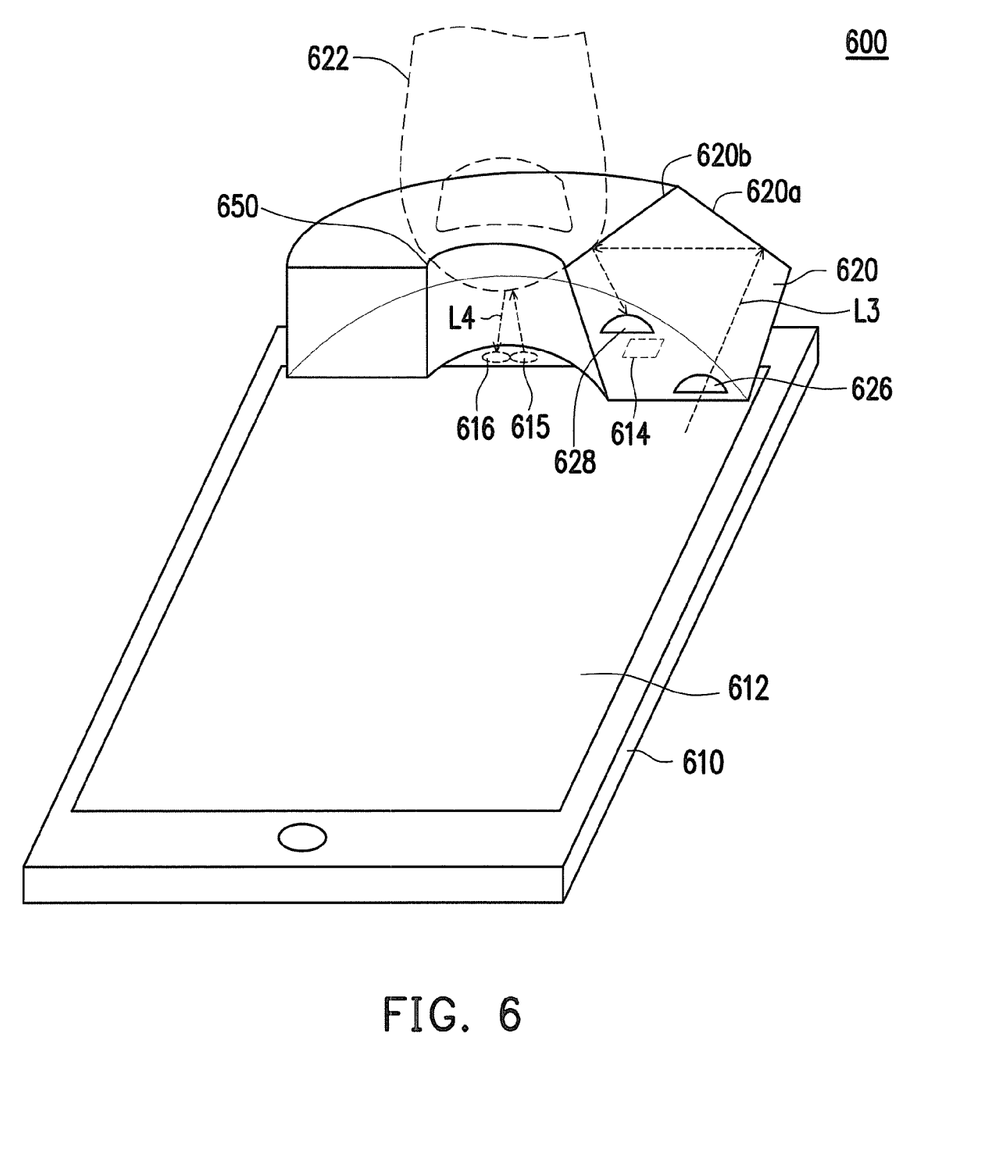
FIG. 6 is a perspective view of a portable analytical device with an optical unit according to a fourth embodiment of the disclosure and an external hand-held computing device.

FIG. 6 is a perspective view of a portable analytical device with an optical unit according to a fourth embodiment of the disclosure. The optical unit 620 includes a sample holder 650, a first reflected surface 620a, a second reflected surface 620b, a first light beam receiving area 626, and a first light beam exiting area 628. The optical unit 620 is aligned to an EHCD 610 which includes a first light beam emitter 612 (e.g. a display), a first light beam receiver 614 (e.g. a camera), a second light beam emitter 615, and a second light beam receiver 616. In the embodiment, for example, the second light beam emitter 615 and the second light beam receiver 616 can be, for example, a proximity sensor of a Smartphone. A light path in the optical unit 620 for a first light beam L3 emitted from the first light beam emitter 612 comprises following sessions: (1) being received in the light beam receiving area 626, (2) illuminating at and reflecting from the first reflected surface 620a, (3) part of the first light beam L3 passing through or reflecting from a sample 622, (4) part of the first light beam L3 reflecting from the second reflected surface 620b, and (5) transmitting to the light beam exiting area 628. The first light beam receiving area 626 and the first light beam exiting area 628 each may further be equipped with a collimator for collimating these light beams. The optical unit 620 is designed such that the first light beam receiving area 626 is aligned to the first light beam emitter 612 such that the first light beam L3 is emitted from the first light beam emitter 612 and received in the first light beam receiving area 626. The first light beam exiting area 628 is aligned to the first light beam receiver 614 such that after the first light beam L3 exits the light beam exiting area 628, the first light beam receiver 614 receives the first light beam L3. Additionally, the first beam light beam emitter 612 radiates the first light beam L3 with a wavelength ranged from 550 nm to 700 nm (or with a white color light). The first light beam receiving area 626 or the first light beam exiting area 628 may equipped with a filtering device to select the specific wavelength of the light beam L3.

The optical unit 620 also provides another light path for a second light beam L4 emitted from the second light beam emitter 615. The light path of the second light beam L4 comprises following sessions: (1) being received from the second light beam emitter 615, (2) illuminating at and being received by the sample 622, and (3) reflecting the second light beam L4 from the sample 622 to be received in the second light beam receiver 616. In the embodiment, the light beam L4 is directly emitted from the second light beam emitter 615 of the EHCD 610 to the sample 622. In the embodiment, the light beams of two different wavelengths are emitted in order to detect signals from both wavelengths. Thus, physiological data such as a level of saturated hemoglobin can be determined. Alternatively, only one light beam emitter may be used to emit just one wavelength, to detect physiological data requiring only one wavelength, or be used to measure the sweetness and saltiness of a sample. Furthermore, the direction of the light path of the light beams L3 and L4 are not normal to the surface of sample holder 650 for the application of refractometer.

Figure 7:
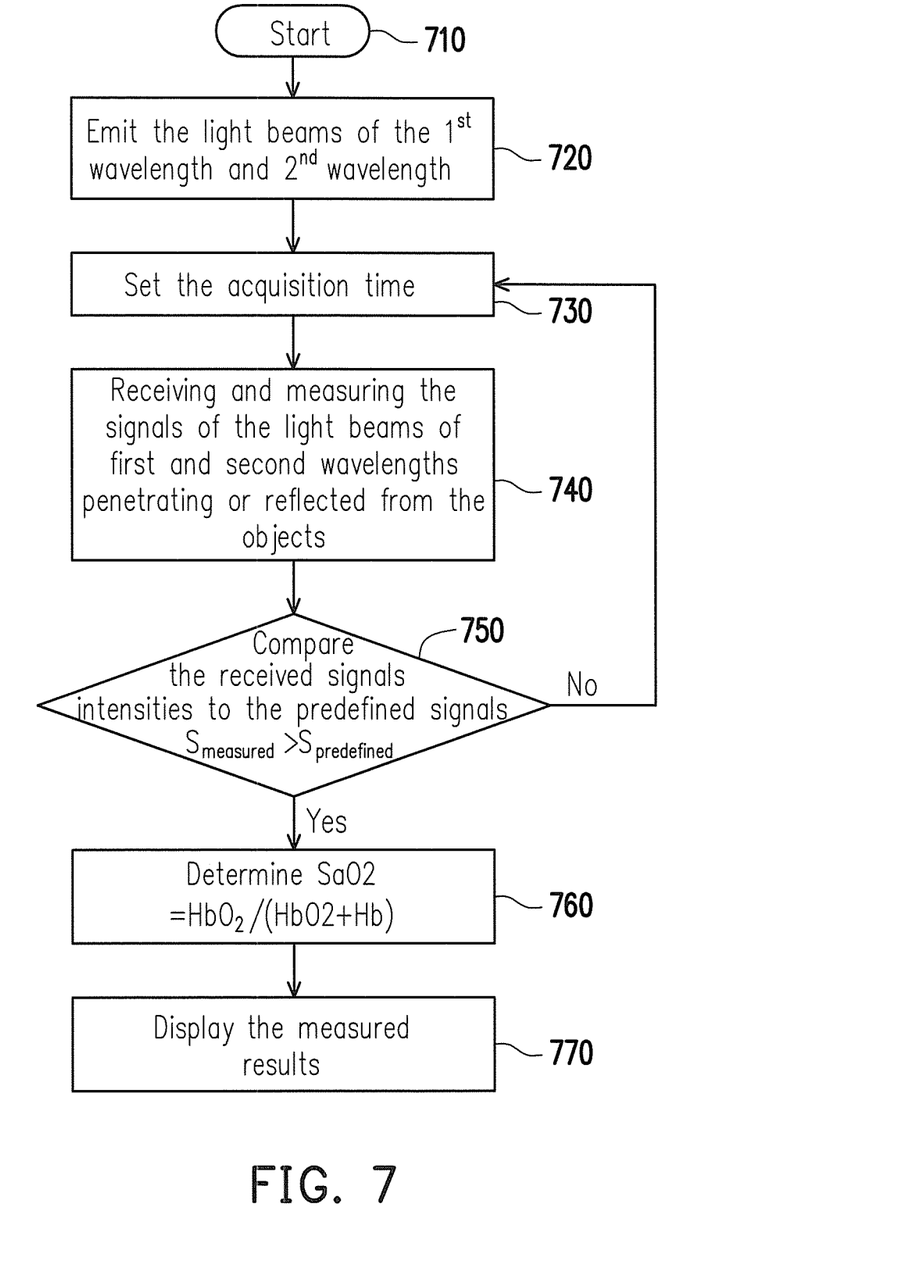
FIG. 7 is a flow diagram of measuring the level of saturated hemoglobin.

FIG. 7 is a flow diagram of measuring the level of saturated hemoglobin according to an embodiment of the disclosure. The method for measuring includes following steps: (1) Two light beams, a first light beam with a first wavelength and a second light beam with a second wavelength, are emitted from an EHCD to at least one sample, such as at least one finger (S720). (2) Waiting for a predetermined acquisition time to collect signals from the sample (S730). (3) A plurality of signals are received from the first light beam and the second light beam after penetrating or being reflected from the sample(s) by a plurality of receivers in the EHCD, wherein a measurement is executed on the EHCD (S740). (4) Light intensities of the received signals are compared with predefined signals (S750). If the intensities of the measured signals are greater than the predefined signals ($S_{measured} > S_{predefined}$), then a level of saturated hemoglobin is calculated by using the formula, $SpO2 = Hb2/(HbO2+Hb)$ (S760). If the intensities are less than the predefined signals, the acquisition time in S730 is extended and the steps from S740 to S750 are repeated. In particular, the predefined signals $S_{predefined}$ are thresholds to ensure the intensity of the measured signals $S_{measured}$ are not just noise signals, but signals received from the light beams. If the intensities of the measured signals are less than the predefined signals, the acquisition time is extended in order to acquire better quality signals. Finally, the results calculated from step S760 (i.e. the level of saturated hemoglobin) are outputted on a display device of the EHCD (S770). Other output device such as through a voice speaker can also be adopted. Alternatively, the step of S730 can be done before step S720.

Figure 8:
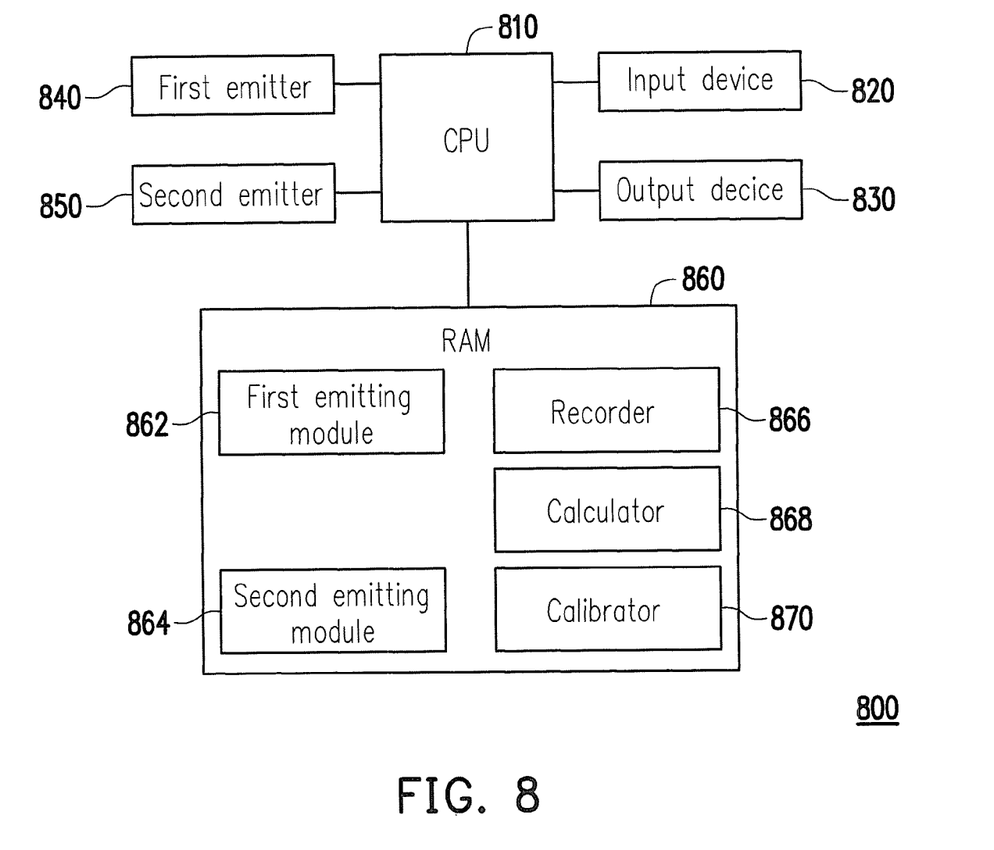
FIG. 8 is a block diagram of a portable analytical system for measuring physiological parameters.

FIG. 8 is a block diagram of a portable analytical system for measuring physiological parameters. According to the above embodiments, a portable analytical system 800 for measuring physiological or sample parameters is provided. The portable analytical system 800 includes an input device 820, such as touch panel, key pad, microphone, etc., for receiving data, a memory unit for storing information 860, an output device 830, such as a display, speaker, etc., for outputting the calculated the parameters, a first emitter 840, a second emitter 850, for emitting different wavelengths of light beams, and a processing unit 810 coupled to the input device 820, the output device 830, the first emitter 840, the second emitter 850, and the memory storing information 860 for controlling the execution of the program routines. The first emitter 840 is, for example, a display of an EHCD of the previous embodiments. The second emitter 850 is, for example, a proximity sensor of an EHCD of the previous embodiments. The memory storing information 860 includes a plurality of program routines. The program routines include: (1) a first emitting module 862 for controlling the first emitter 840 to emit a first light beam with a first wavelength; (2) a second emitting module 864 for controlling the second emitter 850 emitting a second light beam with a second wavelength toward a sample, (3) a recorder 866 for recording a plurality of signals resulted from the first light beam and the second light beam received from the sample with a predetermined duration, and (4) a calculator 868 for calculating a plurality of parameters based on the recorded signals. The memory storing information may further include a calibrator 870 for calibration, to ensure the intensities of the signals reach to predefined signal thresholds. The memory storing information may be a memory device inside the EHCD.

In the embodiment, the input device 820 is, for example, a touch panel or a keyboard of an EHCD of the previous embodiments. The output device 830 is, for example, a display device, a voice speaker, a vibrator, a flasher, a printer, a transmitter, or a combination thereof of an EHCD of the previous embodiments. The first emitter 840 may be the display of the output device 830. However, the first emitter 840 and the output device 830 may also be separate.

In the embodiment, the portable analytical system 800 measures a level of saturated hemoglobin, wherein at least one of the signals received from the sample is a reflected light beam signal. Alternatively, the portable analytical system 800 measures the level of saturated hemoglobin, wherein one of the signals received from the sample is a penetrated light beam signal. The portable analytical system 800 measures the physiological parameters includes saturated hemoglobin value and a heartbeat rate value.

The disclosure further provides a program storage medium, which stores a program for executing various steps of measuring a plurality of physiological parameters. The program performs the steps including: (1) emitting a first light beam with a first wavelength and a second light beam with a second wavelength toward a sample; (2) recording a plurality of signals resulted from the first light beam and the second light beam reflected from the sample with a predetermined duration; (3) calculating the physiological parameters based on the recorded signals, and (4) reporting the calculated physiological parameters to an output device. The program storage medium may be installed in a storage device within the EHCD. The program storage medium installed in the EHCD can be used to obtain physiological data when adapted to the optical unit of the previous embodiments. The EHCD mentioned here includes, for example, a tablet, a portable computer, a wearable device, a watch, or a Smartphone. However, the disclosure is not limited thereto. The program storage medium may be installed in other computing devices for obtaining data.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A portable analytical device, comprising:
    an optical unit for a portable analytical device, comprising:
        a first light beam receiving area;
        a sample holder, for holding a sample;
        a first light beam exiting area; and
        a lens component with a first reflected surface and a second reflected surface, wherein the first reflected surface is adapted to redirect a light path of a first light beam received in the first light beam receiving area to the second reflected surface, and the second reflected surface is adapted to redirect the first light beam to the first light beam exiting area, and the sample holder is located on the light path of the first light beam; and
    an adapting device having a first site for holding an external hand-held computing device (EHCD) and a second site for positioning the optical unit to the EHCD such that the optical unit is aligned with the EHCD.

2. The optical unit for the portable analytical device of claim 1, further comprising:
    a second light beam receiving area, wherein a second light beam is received in a second light beam receiving area; and
    a second light beam exiting area, wherein the second light beam is redirected from the sample holder to the second light beam exiting area, wherein the sample holder is located on a light path of the second light beam.

3. The optical unit for the portable analytical device of claim 1, further comprising:
    a collimator, provided in the first light beam receiving area for collimating the first light beam received in the first light beam receiving area.

4. The optical unit for the portable analytical device of claim 1, further comprising:
    a collimator, provided in the first light beam exiting area for collimating the first light beam redirected from the second reflected surface.

5. The optical unit for the portable analytical device of claim 2, further comprising:
    a collimator, provided in the second light beam receiving area for collimating the second light beam from the second light beam receiving area.

6. The optical unit for the portable analytical device of claim 2, further comprising:
    a collimator, provided in the second light beam exiting area for collimating the second light beam redirected from the sample holder.

7. The optical unit for the portable analytical device of claim 1, wherein the first light beam receiving area receives a light beam emitted from a light beam emitter of an external hand-held computing device (EHCD).

8. The optical unit for the portable analytical device of the claim 7, wherein the wavelength of the first light beam received from the light beam emitter of the EHCD is ranged from about 550 nm to about 700 nm.

9. The optical unit for the portable analytical device of the claim 7, wherein the wavelength of the first light beam received from the light beam emitter of the EHCD is ranged from about 800 nm to about 1000 nm.

10. The optical unit for the portable analytical device of claim 2, wherein the second light beam receiving area receives a light beam emitted from a light beam emitter of an EHCD.

11. The optical unit for the portable analytical device of the claim 10, wherein the wavelength of the second light beam received from the light beam emitter of the EHCD is ranged from about 550 nm to about 700 nm.

12. The optical unit for the portable analytical device of the claim 10, wherein the wavelength of the second light beam received from the light beam emitter of the EHCD is ranged from about 800 nm to about 1000 nm.

13. The optical unit for the portable analytical device of claim 1, wherein the first light beam exiting area is aligned with a light beam receiver of an EHCD.

14. The optical unit for the portable analytical device of claim 2, wherein the second light beam exiting area is aligned with a light beam receiver of an EHCD.

15. The optical unit for the portable analytical device of claim 1, wherein at least one of the first reflected surface and the second reflected surface comprises a transflective surface, a reflective surface, or a combination thereof.

16. The optical unit for the portable analytical device of claim 1, wherein the shape of the sample holder is cylindrical, rectangular, bell-shaped, conical, cubical, pyramidal, or polygonal.

17. The optical unit for the portable analytical device of claim 1, wherein a material of the optical unit comprises mirror-like coating, glass, plastics, quartz, or liquid.

18. The optical unit for the portable analytical device of claim 1, wherein the sample holder couples to at least one of the first reflected surface and the second reflected surface.

19. The optical unit for the portable analytical device of claim 1, wherein the sample holder is located on the light path of the first light beam between the first reflected surface and the second reflected surface.

20. The portable analytical device of claim 1, wherein the second site positions the optical unit to the EHCD so that a first light beam emitter of the EHCD is aligned with the first light beam receiving area, and a first light beam exiting area is aligned with a first light beam receiver of the EHCD.

21. The portable analytical device of claim 1, wherein the optical unit further comprises:
at least one collimator located on the light path of the first light beam.

22. The portable analytical device of claim 1, wherein the first light beam is emitted from the first light beam emitter of the EHCD.

23. The portable analytical device of claim 1, wherein the optical unit further comprises:
a second light beam receiving area, wherein a second light beam is received in a second light beam receiving area; and
a second light beam exiting area, wherein the second light beam is redirected from the sample holder to the second light beam exiting area, wherein the sample holder is located on a light path of the second light beam.

24. The portable analytical device of claim 23, wherein the second light beam is emitted from a second light beam emitter of the EHCD.

25. The portable analytical device of claim 23, wherein the optical unit further comprises:
at least one collimator located on the light path of the second light beam.

26. The portable analytical device of the claim 23, wherein a wavelength of the first light beam from the EHCD is ranged from about 550 nm to about 700 nm.

27. The portable analytical device of claim 23, wherein a wavelength of the second light beam from the EHCD is ranged from about 800 nm to about 1000 nm.

28. The portable analytical device of claim 1, wherein at least one of the first reflected surface and the second reflected surface comprises a transflective surface, a reflective surface, or a combination thereof.

29. The portable analytical device of claim 1, wherein the portable analytical device is a refractometer for analyzing at least one of a sweetness and a saltiness of a sample.

30. The portable analytical device of claim 1, wherein the portable analytical device is an oximeter for analyzing at least one of a saturated hemoglobin and a heartbeat rate.

31. The portable analytical device of claim 1, wherein a shape of the sample holder is cylindrical, rectangular, bell-shaped, conical, cubical, pyramidal, or polygonal.

32. The portable analytical device of claim 1, wherein the sample holder is coupled to at least one of the first reflected surface and the second reflected surface.

33. The portable analytical device of claim 1, wherein the EHCD comprises a tablet, a portable computer, a wearable device, a watch, or a Smartphone.

* * * * *